United States Patent [19]
Brown et al.

[11] Patent Number: 5,348,549
[45] Date of Patent: Sep. 20, 1994

[54] FLUID TIGHT MEDICAL APPARATUS DISPOSAL RECEPTACLE

[76] Inventors: Daniel R. Brown, 16593 Nina Cir., Omaha, Nebr. 68130; Rodney Laible, R.R. 1, Box 37, Bennington, Nebr. 68007

[21] Appl. No.: 38,827

[22] Filed: Mar. 29, 1993

[51] Int. Cl.$^5$ .................. A61B 19/00; B65D 51/18
[52] U.S. Cl. .................. 604/403; 220/254; 220/306; 220/908
[58] Field of Search ............. 604/403; 220/908, 254, 220/306, 229; 215/263

[56] References Cited

U.S. PATENT DOCUMENTS

| | | | |
|---|---|---|---|
| 1,454,836 | 5/1923 | Slocomb . | |
| 2,839,229 | 6/1958 | Scheswohl | 222/567 |
| 2,882,947 | 4/1959 | Close | 150/5 |
| 3,315,402 | 4/1967 | Scott et al. | 220/229 |
| 3,355,056 | 11/1967 | Fisch | 220/42 |
| 3,446,391 | 5/1969 | Yates, Jr. | 220/60 |
| 3,527,372 | 9/1970 | Manning | 220/40 |
| 3,762,673 | 10/1973 | Koslovsky | 604/403 |
| 3,941,268 | 3/1976 | Owens | 215/216 |
| 4,371,092 | 2/1983 | Teague | 220/324 |
| 4,380,304 | 4/1983 | Anderson | 220/306 |
| 4,444,332 | 4/1984 | Widen et al. | 220/306 |
| 4,453,646 | 6/1984 | Harrild | 220/258 |
| 4,555,042 | 11/1985 | Rathbun | 220/306 |
| 4,560,081 | 12/1985 | Adams | 220/306 |
| 4,715,498 | 12/1987 | Hanifl | 206/366 |
| 4,733,794 | 3/1988 | Kent | 220/306 |
| 4,746,008 | 5/1988 | Heverly et al. | 220/306 |
| 4,759,466 | 7/1988 | Chase et al. | 220/306 |
| 4,762,248 | 8/1988 | Uhlig | 220/306 |
| 4,874,103 | 10/1989 | Quisenberry et al. | 220/306 |
| 4,915,251 | 4/1990 | Payne | 220/306 |
| 5,088,614 | 2/1992 | Dumestre | 220/254 |
| 5,114,421 | 5/1992 | Polak | 604/403 |
| 5,156,291 | 10/1992 | Mielke | 220/254 |
| 5,165,563 | 11/1992 | McKendry | 220/306 |
| 5,165,564 | 11/1992 | Prout et al. | 220/254 |
| 5,235,795 | 8/1993 | De Busk | 220/254 X |
| 5,295,602 | 3/1994 | Swanson | 220/306 |

Primary Examiner—Randall L. Green
Assistant Examiner—Elizabeth M. Burke
Attorney, Agent, or Firm—John A. Beehner

[57] ABSTRACT

A medical apparatus disposal container includes an open topped container adapted to be closed by a lid having a top wall with an opening through which medical apparatus may be disposed into the container. A cap is provided for closing the opening when the container is filled. A continuous seal is effected between the lid and container by a pair of generally parallel spaced apart interior and exterior flanges defining an open bottom channel around the periphery of the lid. The channel is of a size and shape to receive the upper portion of the container sidewall in fluid tight sealed relation therein with the interior flange extending downwardly into the container. Coacting fasteners on the lid and container sidewall secure the lid in sealed relation onto the container. The lid may be fitted with a sealing gasket or flexible flange in the open bottom channel to effect further sealing of the lid.

16 Claims, 4 Drawing Sheets

FLUID TIGHT MEDICAL APPARATUS DISPOSAL RECEPTACLE

BACKGROUND OF THE INVENTION

The present invention is directed generally to a container for disposing of various medical apparatus, such as sharps and chemotherapy equipment, and more particularly to a fluid tight disposal container for such medical apparatus, Due in part to concern about spread of infectious diseases, such as AIDS, hepatitis, and the like, the general practice is to dispose of used sharps, such as medical syringes, needles and the like, in relatively rigid walled sealed sharps containers so that those handling the containers will be protected from puncture by the potentially infectious sharps and so that the contents will not contaminate the environment after disposal. Whereas existing sharps containers provide secure containment of the sharps, they are generally not designed to be fluid tight. Accordingly, such containers are ill-suited for disposal of fluid container apparatus, such as chemotherapy equipment, including the needles, tubes, and bags. Furthermore, in several countries outside of the United States, sharps containers are required to be leakproof or leak resistant with the result that conventional sharps containers are unsuitable for foreign markets.

One known sharps container has a gasket installed in the lid for sealed engagement against the top of the container, but the provision and installation of the separate gasket adds to the expense of the container without providing a reliable fluid tight seal. Additionally, several of the presently available containers require abundant force to close the lid. Another major drawback of presently available containers is the inability to visually inspect that the lid has been secured. Furthermore, some current containers are round in shape which is not conducive to efficient storage of elongated objects such as syringes and the like.

Accordingly, a primary object of the present invention is to provide a fluid tight medical apparatus disposal container.

Another object is to provide such a container wherein the lid requires no separate gasket for effecting a reliable leak resistant seal onto the container.

Another object is to provide such a container that when fitted with a gasket becomes leak proof.

Another object is to provide such a container wherein the lid includes an interior sealing flange adapted for insertion into the container to properly guide the lid and its fasteners onto the container.

Another object of the present invention is to provide a container, the lid sealing engagement of which may be visually verified.

Another object of the present invention is to provide a container which is sized and shaped for efficient storage of medical apparatus such as syringes and the like and such that the containers may be easily stacked for storage, or placed under vent hoods where various chemicals are mixed.

Another objective is to provide such a container wherein the container is capable of maintaining a seal with the lid even where the lid is subjected to slight vertical movement relative to the base of the container.

Another object is to provide a container which may be sealed by application of pressure at a single location instead requiring pressure throughout the perimeter of the container.

Another object is to provide such a container wherein the lid provides a fluid tight seal even if the lid is not fully installed onto the container with all fasteners engaged.

Another object is to provide such a container including a lid and cap having coacting locking means such that the cap is locked onto the lid upon insertion of the cup locking tabs.

Another object is to provide such a container which is capable of easy stacking and nesting of such containers, in the hospital environment or in shipping.

Another object is to provide such a container which is simple and rugged in construction, economical to manufacture and efficient in operation.

SUMMARY OF THE INVENTION

The medical apparatus disposal container of the present invention includes an open topped container having a lid adapted to be closed and sealed onto a peripheral upper portion of the container sidewall. The lid includes a top wall having an opening through which medical apparatus may be disposed of into the container, a closure cap for the opening and means for sealing the lid onto the upper portion of the container sidewall. Coacting fasteners are provided on the lid and container sidewall for securing the lid in sealed relation onto the container in the fully installed position of the lid. The sealing means on the lid include a pair of generally parallel, spaced apart interior and exterior flanges defining an open bottom channel around the periphery of the lid. The channel is of a size and shape to receive the upper portion of the container sidewall in fluid tight sealed relation therein, with the interior flange extending downwardly into the open topped container.

The upper portion of a container sidewall has an interior surface for guiding the interior flange of the lid into the container. That interior flange is of a size and shape to form a continuous seal with the interior surface of the upper portion of the sidewall even before the lid is fully depressed onto the container with all fasteners engaged. If certain fasteners are accidentally left unengaged or if one corner of the lid is not fully pressed onto the container, a fluid tight seal is nevertheless achieved between the lid and container. This is partially due to an interference fit between the interior flange of the lid and the interior surface of the container. The exterior flange of the lid has an interior surface which preferably conforms to the exterior surface of the upper portion of the container sidewall to afford continuous contact along the engaged surfaces thereof. A plurality of hooks and eyelets may be formed on the lid and container for securing the lid in snap fit relation onto the container in the fully installed position of the lid. A bead may be formed on the exterior surface of the sidewall upper portion to provide additional blockage of any capillary fluid flow between the engaged surfaces of the lid and container. Finally, the closure cap and chimney onto which it is fastened are provided with lock tabs and tab receiving openings so that the cap may be locked onto the container.

In an alternative embodiment, a gasket of rubber material or the like is positioned in and throughout the open bottom channel defined by the interior and exterior flanges on the lid. Such a gasket provides a leakproof seal when the lid is pressed onto the container.

In a second alternative embodiment, a flexible sealing flange is placed in and throughout the open bottom channel and protruding outwardly therefrom. When the lid is pressed onto the container, the flexible flange engages the container sidewall top, forming a leak resistant seal.

DESCRIPTION OF THE PREFERRED EMBODIMENT

Figure 1:
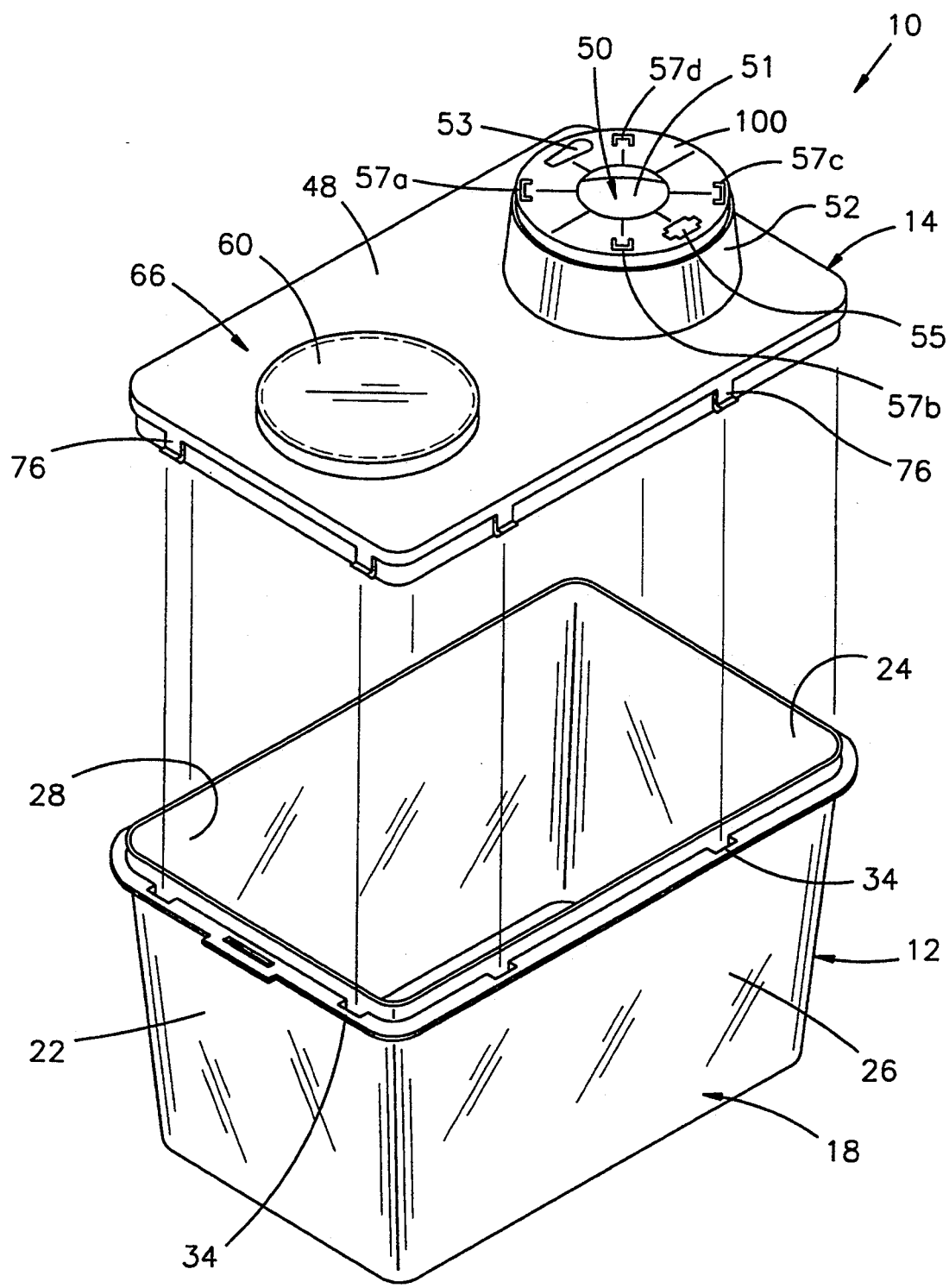
FIG. 1 is an exploded perspective view of the sharps container with the cover in spaced relation above the container and prior to assembly.

The medical apparatus disposal receptacle 10 of the present invention is illustrated in the drawings as including an open topped container 12 adapted to be closed by a lid 14. Container 12 has a bottom wall 16 connected to a peripheral sidewall 18 end walls 22 and 24 and back wall 28 to define a fluid containing receptacle.

Figure 2:
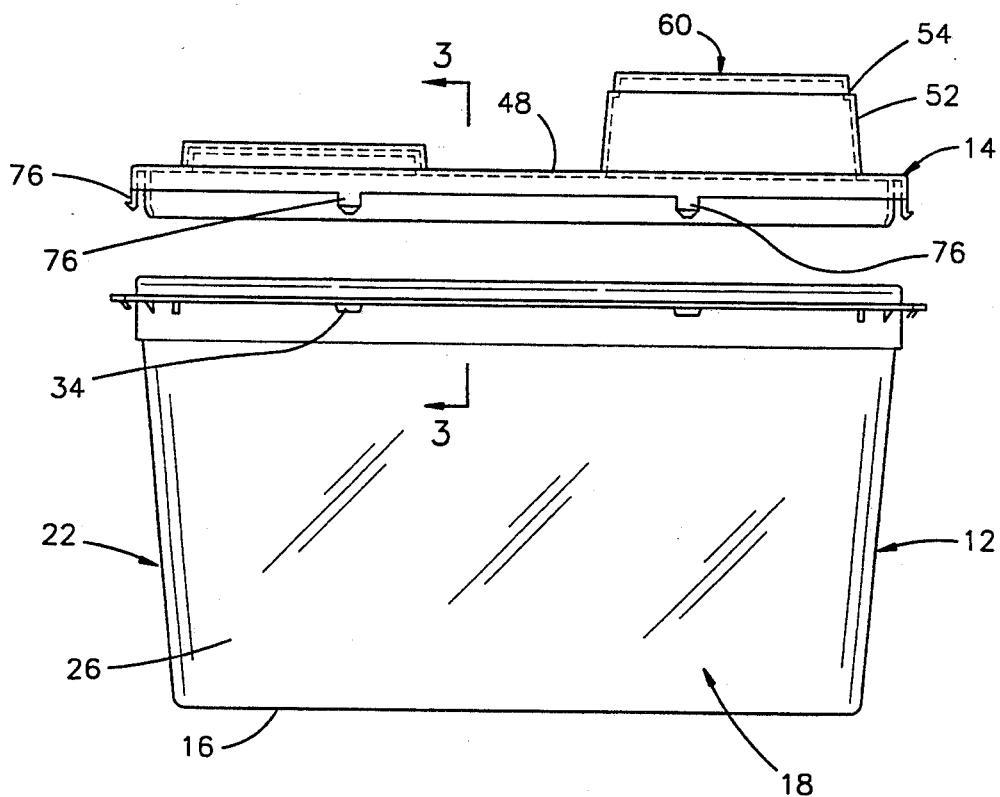
FIG. 2 is a side elevational view of the cover and container with hidden portions of the cover indicated in dotted lines.
Figure 3:
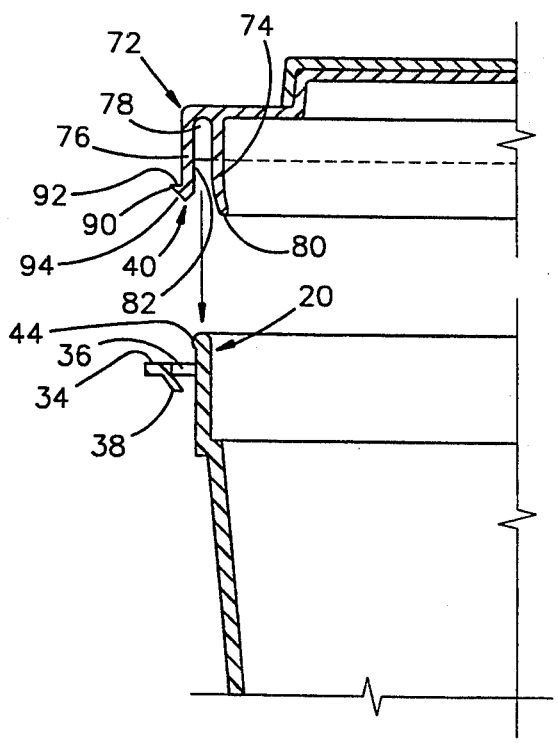
FIG. 3 is an enlarged partial sectional view taken along line 3—3 in FIG. 2.

The container sidewall 18 has an upper portion 20 adapted for engagement with the lid 14. As seen in FIG. 2, the ends 22 and 24 as well as the front and back surfaces 26 and 28 of sidewall 18 slightly taper upwardly and outwardly to facilitate nesting of several containers for space efficient transport and storage. As shown best in FIG. 3, the interior surface of upper portion 20 is generally vertical and the lower most edge 80 of interior flange 74 from a vertical plane to have somewhat of a funnel effect for guiding the lid onto and into the container.

Protruding exteriorly from sidewall upper portion 20 are eight hook receiving eyelets 34, arranged two on each end of the container and two on each of the front and back surfaces, as shown in FIG. 1. The specific number of eyelets is not critical to the invention, but eight are believed to be sufficient to secure lid 14 onto container 12. Each eyelet 34 defines an opening 36 and has a latch 38 protruding downwardly and interiorly from an exterior portion of the eyelet to cooperatively engage a respective hook 40 on lid 14 as described below.

Finally, a continuous, exteriorly protruding bead 44 is formed on the exterior surface and at the top of sidewall upper portion 20 for further sealing engagement with the lid as described below.

Lid 14 includes a transversely extended top wall 48 having a relatively large opening 50 through which medical apparatus may be disposed of into the container 12. In the preferred embodiment, the opening 50 is surrounded by a raised chimney 52 which, among other things, protects the hands of medical personnel using the device from contacting sharps or other waste previously disposed of in the container 12. Chimney 52 is interiorly stepped at 54 to define a lip for receiving a cap 60 thereon.

Sitting atop raised chimney 52 is a surface 100 having a plurality of openings therethrough. Opening 51 provides a means for receiving larger objects such as bags, tubing, syringes and the like. Smaller openings 53 and 55 are sized and shaped to allow needles to be disengaged from syringes in a conventional manner, and disposed of without the need for physical contact with the needle. Sockets 57a–d provide a means for receiving cap hooks (not shown) and securing the cap 60 into position in a conventional manner. Other conventional means might be used to secure the cap 60 onto chimney 52 such as screws, latching tabs or the like.

So that opening 50 may be opened for the disposal of relatively large medical apparatus into container 12, cap 60 is removable from chimney 52 and may be stored on a raised tower portion 66 on top wall 48. Tower portion 66 provides conventional means for storage of cap 60 while objects are disposed of through opening Whereas the size or diameter of opening 50 is not critical to the invention, it is preferable that the opening be large enough to accommodate relatively large medical apparatus, such as the bag, tubing and needle used for chemotherapy. A 110 millimeter opening will accommodate such materials. The step 54 in chimney 52 is advantageous for eliminating any exterior protrusion of the cap from the chimney which could catch on foreign matter and potentially cause cap 60 to be pried from chimney 52.

The exterior periphery of lid 14 is formed as a seal 72 including a pair of generally parallel spaced apart interior and exterior depending flanges 74 and 76 which cooperate to define an open bottom channel 78 around the periphery of lid 14. The channel is of a size and shape to receive upper portion 20 of the container sidewall be in fluid tight sealed relation therein, with the interior flange 74 extending downwardly into the container 12.

Interior flange 74 protrudes downwardly to a slightly greater extent than exterior flange 76 to facilitate guiding the lid into and onto container 12. The lowermost edge 50 of interior flange 74 is tapered downwardly and interiorly to cooperate with the container sidewall above bend line 30 for guiding interior flange into the open top of container 12. Above edge 80, interior flange 74 is of a size and shape to form a continuous seal with the interior surface of the container sidewall upper portion 20 as shown in its fully installed position shown in FIG. 4. The lid and container are dimensioned so as to provide an interference fit, dimensionally on the order of approximately three or four thousandths of an inch. Accordingly, the interior flange 74 engages sidewall 18, forming a continuous peripheral seal therewith even prior to full seating of the lid 14 onto the container.

Figure 4:
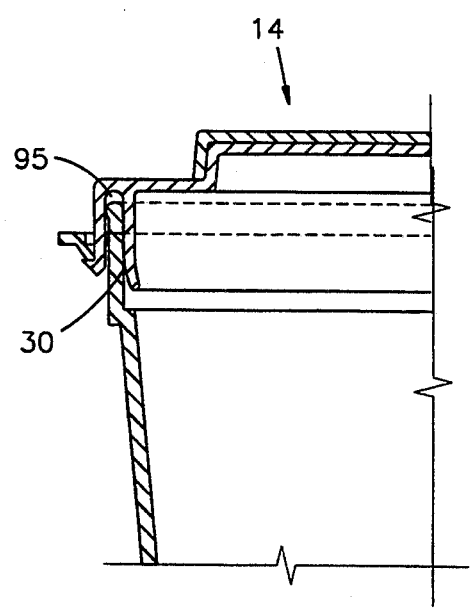
FIG. 4 is an end sectional view similar to FIG. 3 but with cover assembled onto the container.

The exterior flange 76 has a substantially interior flat surface 82 which substantially conforms to the exterior surface of the container sidewall upper portion 20 when the lid is fully installed onto the container as shown in FIG. 4. In this regard, the inclination of the interior surface 82 approximates that of the exterior surface of sidewall upper portion 20. Bead 44 located on the exterior surface of side wall upper portion 20 makes contact with the interior surface 82 of flange 76 as soon as installation of lid 14 begins, due to the dimensioning of the interior flange 74, exterior flange 76 and the protrusion of bead 44. Consequently, a seal may be formed even if the lid 14 is not uniformly locked completely in the down position throughout the perimeter of the lid. The coacting bead 44 and flange 76 are effective to stop capillary fluid flow around the bead, thereby providing a leak resistant seal between the lid 14 and the container 12. Such a seal meets government and industry standards for sealing of medical containers for example those of the British government.

At eight locations around the periphery of lid 14, corresponding to the positions of eyelets 34, the exterior flange 76 is extended downwardly to form integral hooks 40, each having a foot 90 on the lower end which presents a generally horizontal top surface 92 and downwardly and interiorly tapered bottom surface 94 to facilitate entry of the hook 40 into the respective eyelet 34. Upon entry of the hook through an eyelet 34, tapered bottom surface 94 deflects latch 38 outwardly until the lid is seated in its fully installed position whereupon the latch 38 snaps back for engaging the hook top surface 92 for securely fastening the lid in its fully installed position. The latch 38 and hook 40 design provides a quick visual confirmation of the sealing status of lid 12. It will be noted in FIG. 4 that when lid 14 is in its fully installed position, a space 95 remains between sidewall upper portion 20 and open bottom channel 78. In an alternative embodiment described below, this space may be filled by a gasket, or flange effecting a greater degree of sealing between the lid 14 and container 12.

Receptacle 10 is preferably formed of a plastic material In the preferred embodiment, the container 12 and lid 14 are formed of dissimilar materials, with the container being of a harder material such as homopolymer polypoplayne to resist penetration by needles contained therein. The top may be a softer material, such as a copolymer propylene having the soft ethylene mixed into it. The softer top material also facilitates the effective sealing of the top onto the container sidewall. The container 12 and lid 14 may be formed by injection molding which is generally cheaper than blow molding and permits the components to be manufactured to greater tolerances. Additionally, in the preferred embodiment, the receptacle 10 is rectangular in shape, thereby permitting more efficient storage of elongated medical instruments such as syringes, needles, and the like.

In operation, an operator takes a container 12 from a nested stack of containers, places a lid 14 over it so that the fastener hooks 40 of the lid are aligned with the container eyelets 34, whereupon the lid is pressed downwardly onto the container. As shown best in FIG. 4, an effective continuous seal is formed between the interior flange 74 and sidewall upper portion 20 and between bead 44 and flange 76, even before the lid is fully depressed onto the sidewall to its fully installed position. Thus, if an operator in a hurry latches only the majority of the hook and eyelet fasteners, leaving one or more unfastened, a continuous seal of the lid onto the container is nevertheless made. Along the same line, the elongated length of the interior flange 74 of lid 14 and its lower most tapered edge 80 greatly facilitate guiding of the lid into the container and aligning the hooks 40 and eyelets 34. The flexibility and interference fit dimensions of the interior flange 74 relative to container sidewall upper portion 20 assure the required fluid tight seal. The elongated engagement surfaces between the lid flanges and sidewall upper portion 20 in the fully installed position of the lid, coupled with the coacting bead 44 and flange 76, prevent even capillary fluid flow from the container.

When the container 12 is filled with discarded medical apparatus, cap 60 is simply lifted from tower portion 66, whereupon the cap 60 is placed on chimney 52 with its hooks (not shown) being inserted in openings 57a–d and in surface 100 to seal cap 60 over the open top 51 of chimney 52. The sealed receptacle 10 is then disposed of in the manner provided for potentially infectious waste.

Figure 5:
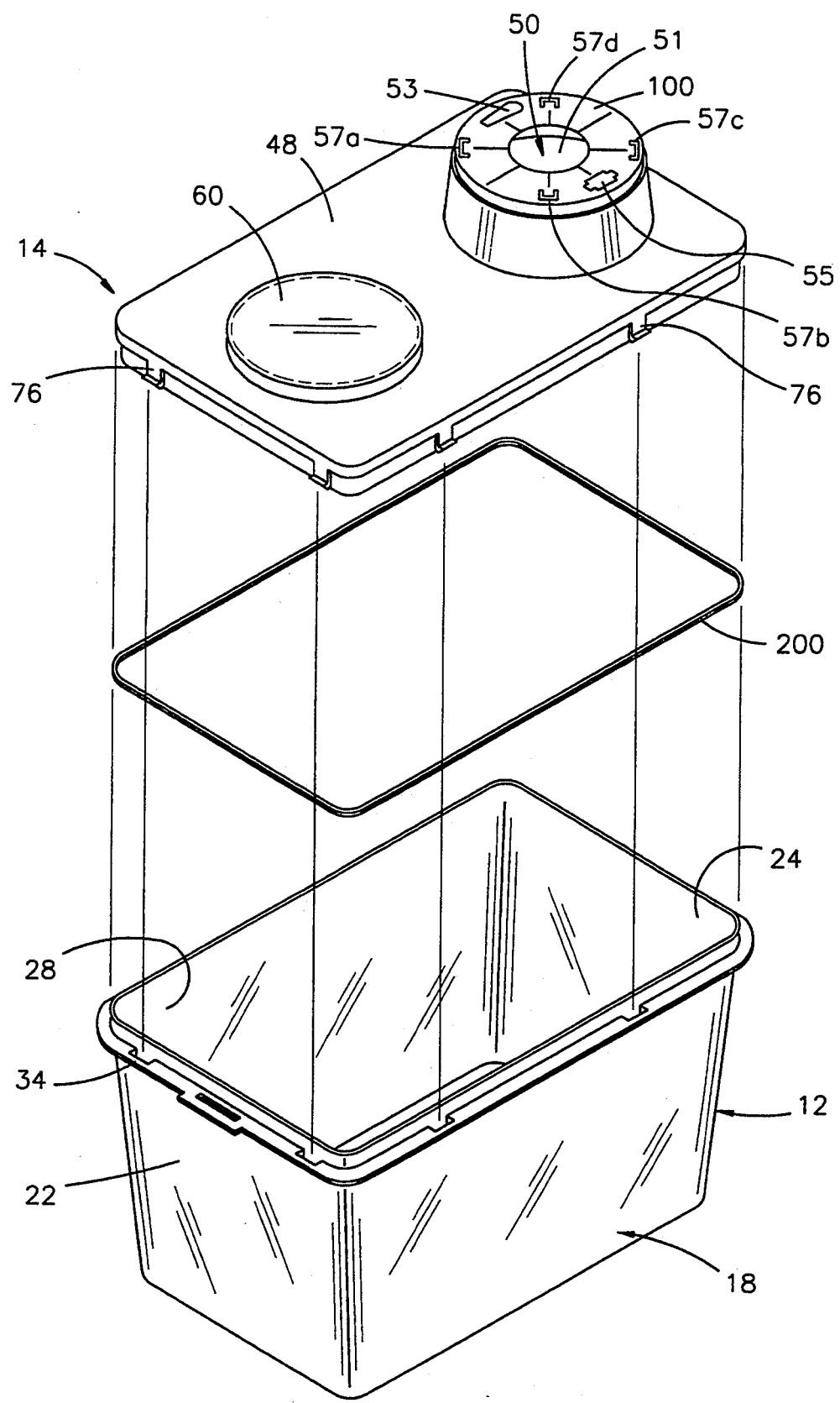
FIG. 5 is an exploded perspective view of an embodiment of the invention including a gasket for insertion between the cover and container.
Figure 6:
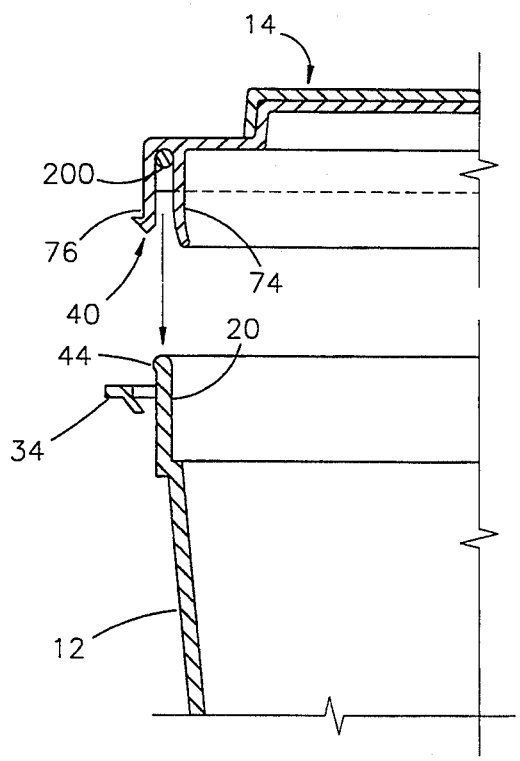
FIG. 6 is an enlarged partial sectional view of the container and cover prior to assembly with the gasket installed in the cover.
Figure 7:
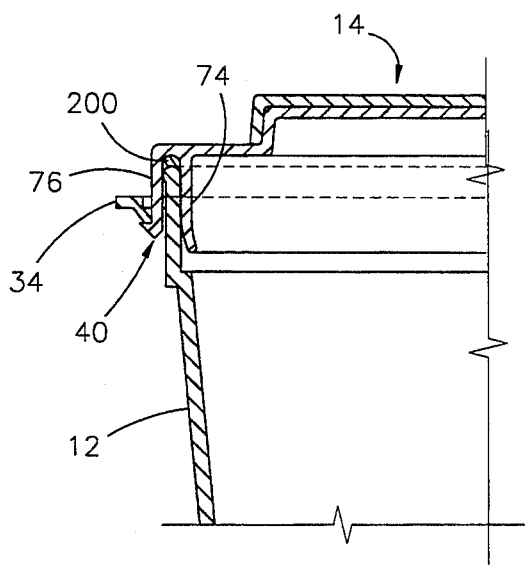
FIG. 7 is a partial sectional view, similar to FIG. 6 but with the cover assembled onto the container compressing the gasket material therebetween.

In an alternative embodiment, shown in FIGS. 5, 6, and 7, a continuous gasket 200 is installed in and throughout the open bottom channel 78 formed by interior flange 74 and exterior flange 76. Gasket 200 is of a size and shape so as to be slightly larger than the space formed between the top of sidewall upper portion 20 and the open channel 78, when the lid is fully installed. As shown most clearly in FIG. 7, when lid 14 is placed on container 12 and hooks 40 fully inserted in to eyelets 34, gasket 200 is compressed slightly by the top of sidewall upper portion 20 such a fluid tight, leak proof seal is formed. Further additional seals are provided as before, between the interior flange 74 and the interior surface 82 of sidewall upper portion 20 and between bead 44 and the interior surface of exterior flange 76. As in the original embodiment, these two seals provide a leak resistant seal even if the lid is not uniformly fully locked into position. The slight oversizing of gasket 200, in conjunction with its flexibility, allows the seal to be maintained in-spite of irregularities in the top of sidewall upper portion 20. In the preferred embodiment, gasket 200 is manufactured of thermoplastic rubber material such as the HYSEAL brand, but may be any similar material.

Figure 8:
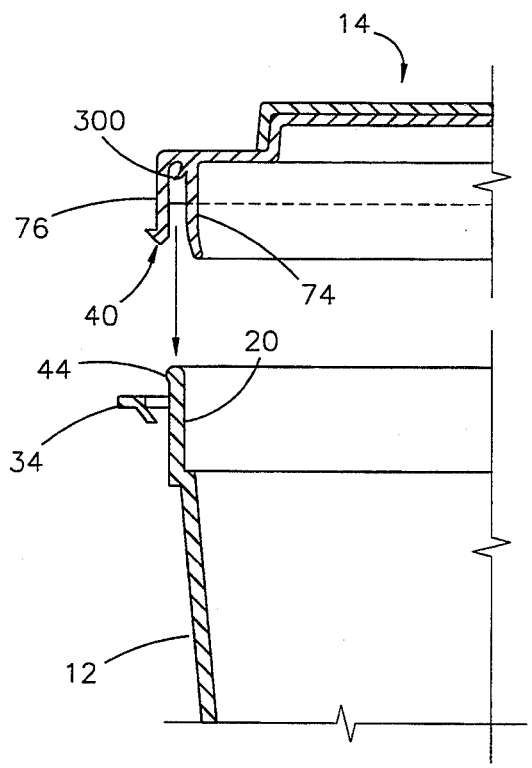
FIG. 8 is a partial sectional view of a third embodiment wherein the cover includes a sealing flange for engagement with the rim of the container.
Figure 9:
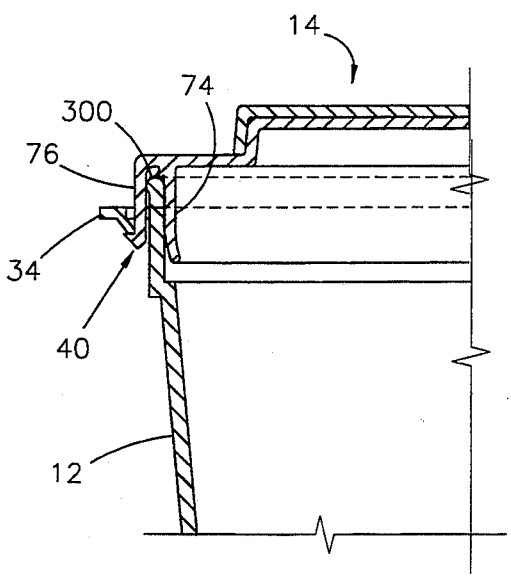
FIG. 9 is a partial sectional view, similar to FIG. 8 but with the cover assembled onto the container and the sealing flange engaging the rim of the container.

In an additional alternative embodiment, shown in FIGS. 8 and 9, a continuous, flexible sealing flange 300 is installed and throughout in open bottom channel 78 formed by interior flange 74 and exterior flange 76. Flange 300 is deflected upward by contact with the top of sidewall upper portion 20. Additional sealing means provided by bead 44 and flange 76 and flange 74 and sidewall upper portion 20 continue to provide additional sealing and in the event the lid is not fully locked down so as to contact flange 300 throughout its length, these additional means provide a leak resistant seal.

Whereas the invention has been shown and described in connection with a preferred embodiment thereof, it is apparent that modifications, additions and substitutions may be made which are within the intended broad scope of the appended claims. For example, the number and positioning of hooks and eyelets may be varied as desired. A gasket may be provided inside cap 60 to alternately assure sealed closing of chimney 52.

Thus there has been shown and described a medical apparatus disposal container which accomplishes at least all of the stated objects.

We claim:

1. A medical apparatus disposal container, comprising, an open topped container having a bottom wall and peripheral side wall interconnected to define a receptacle for fluids, said peripheral sidewall having an upper portion, having interior and exterior surfaces a lid for said container, said lid having a periphery and comprising, a top wall having an opening through which medical apparatus may be disposed into said container;

means for closing said opening upon filling said container with medical apparatus;

sealing means for sealing said lid onto the upper portion of said sidewall;

coacting fasteners on said lid and container sidewall, said fasteners being operative to secure said lid in sealed relation on the upper portion of said sidewall in a fully installed position, said sealing means comprising a pair of generally parallel spaced apart interior and exterior flanges depending from said lid to wall and defining an open bottom channel around the periphery of said lid, said channel being of a size and shape to receive the upper portion of said container sidewall in fluid tight sealed relation therein with said interior flange extending downwardly into said container, said interior flange having a vertical depth greater than that of said exterior flange whereby insertion of said interior flange into said upper portion of said container sidewall is greatly facilitated.

2. The medical apparatus disposal container of claim 1 wherein said interior flange is of a size and shape to form a continuous seal with the interior surface of said upper portion of the sidewall at a position of the lid above its fully installed position in which said coacting fasteners are operatively engaged.

3. The medical apparatus disposal container of claim 2 further comprising a bead on the exterior surface and substantially at the top of said upper portion of said container sidewall arranged for engagement with the interior surface of said exterior flange.

4. The medical apparatus disposal container of claim 3 wherein said exterior flange has an interior surface which substantially conforms to the exterior surface of the upper portion of said sidewall.

5. The medical apparatus disposal container of claim 2 wherein said interior flange and interior surface of said upper portion of the sidewall are of a size and shape to provide an interference fit therebetween in the fully installed position of said lid.

6. The medical apparatus disposal container of claim 5 wherein a gasket is positioned between said interior and exterior flanges, adjacent and throughout said open bottom channel such that when said lid is in the fully installed position, said gasket is in fluid sealing contact with the top of said side wall upper portion.

7. The medical apparatus disposal container of claim 6 wherein said gasket is of a size and shape which allows said gasket to contact said top of said side wall upper portion prior to the lid achieving a fully installed position such that sealing contact is made in spite of irregularities in the top of said side wall upper portion.

8. The medical apparatus disposal container of claim 7 wherein said gasket is a rubber material.

9. The medical apparatus disposal container of claim 3 further comprising a flexible flange connected between and adjacent said interior and exterior flanges substantially at said open bottom channel and extending outwardly therefrom, and through the channel such that when said lid is in the fully installed position, fluid sealing contact is made between said flange and the top of said side wall upper portion.

10. The medical apparatus disposal container of claim 9 wherein said flexible flange is sized and constructed of a material such that said flange is bent away from said interior flange in response to contact with said side wall upper portion top and increasing the surface area contacted.

11. The medical apparatus disposal container of claim 1 wherein said coacting fasteners comprise a plurality of hooks and eyelets arranged in vertically registered relation on said lid and container.

12. The medical apparatus disposal container of claim 11 wherein said hooks are integrally formed downward projections on the exterior flange of said lid.

13. The medical apparatus disposal container of claim 12 wherein said eyelets are integrally formed on said container sidewall for receiving said hooks in snap fit relation therein in the fully installed position of said lid on said container.

14. The medical apparatus disposal container of claim 1 wherein said lid top wall includes a raised chimney portion around said opening and said means for closing said opening comprises a closure cap adapted to fit onto said chimney portion.

15. The medical apparatus disposal container of claim 14 wherein said cap includes a plurality of locking members and wherein said chimney portion includes a top having openings to receive and retain said cap locking members, securing said cap into place.

16. The medical apparatus disposal container of claim 15 wherein said lid further comprises a raised tower portion for storage of said closure cap at a position displaced from said opening.

* * * * *